United States Patent [19]
Takano et al.

[11] Patent Number: 5,646,013
[45] Date of Patent: *Jul. 8, 1997

[54] METHOD OF PRODUCING FOREIGN GENE PRODUCTS

[75] Inventors: Toshiya Takano, Saitama; Minoru S.H. Ko, Chiba, both of Japan

[73] Assignee: Daiichi Seiyaku Co., Ltd., Tokyo, Japan

[*] Notice: The term of this patent shall not extend beyond the expiration date of Pat. No. 5,534,419.

[21] Appl. No.: 495,838

[22] Filed: Jun. 28, 1995

Related U.S. Application Data

[63] Continuation of Ser. No. 139,877, Oct. 22, 1993, abandoned, which is a continuation of Ser. No. 841,269, Feb. 26, 1992, abandoned, which is a continuation of Ser. No. 269,044, Nov. 9, 1988, abandoned.

[30] Foreign Application Priority Data

Nov. 9, 1987 [JP] Japan ................... 62-282893

[51] Int. Cl.$^6$ ............... C12N 15/00; C12N 5/00; C12N 1/38; C12P 21/06
[52] U.S. Cl. .............. 435/69.1; 435/172.3; 435/244; 536/23.1; 536/24.1
[58] Field of Search ................ 536/23.1, 24.1; 435/69.1, 240.2, 244, 172.3

[56] References Cited

U.S. PATENT DOCUMENTS 4,374,927  2/1983  Sninsky ................... 435/68

FOREIGN PATENT DOCUMENTS

| 0043980 | 1/1982 | European Pat. Off. . |
| 0105141 | 4/1984 | European Pat. Off. . |
| 0213628 | 3/1987 | European Pat. Off. . |
| 0219214 | 4/1987 | European Pat. Off. . |
| 8800975 | 2/1988 | European Pat. Off. . |
| 8803168 | 5/1988 | European Pat. Off. . |

OTHER PUBLICATIONS

Ko & Takano, DNA 8, 127 (1989).
Ko et al., Gene 84 (1989).
Lee et al., Nature 294:228–232 (1981).
Hynes et al., PNAS 80:3637 (1983).
Majors & Varmus, PNAS 80:5866–5870 (1983).
Vanderbilt et al., Chem. Abs. vol. 107:89:70998h (1987).
Meisfeld et al., Cell 46:389–399 (1986).

*Primary Examiner*—Suzanne E. Ziska
*Attorney, Agent, or Firm*—Sughrue, Mion, Zinn, Macpeak & Seas

[57] ABSTRACT

A method of producing foreign gene products which comprises (1) transforming animal cells either (a) by using two plasmids, namely a plasmid containing the MMTV LTR and a foreign gene encoding a physiologically active substance inserted therein downstream from the LTR and a plasmid containing the LTR and a glucocorticoid receptor protein gene inserted therein downstream from the LTR, or (b) by using one plasmid comprising the LTR, a glucocorticoid receptor protein gene located downstream from the LTR, another LTR and a foreign gene encoding a physiologically active substance located downstream from the latter LTR, and (2) cultivating the transformed animal cells in a medium containing glucocorticoid in an amount effective for inducing mRNA transcription.

5 Claims, 4 Drawing Sheets

METHOD OF PRODUCING FOREIGN GENE PRODUCTS

This is a continuation of application Ser. No. 08/139,877 filed 22 Oct. 1993 now abandoned, which is a continuation of Ser. No. 07/841,269 filed 26 Feb. 1992, abandoned, which is a continuation of Ser. No. 07/269,044 filed 9 Nov. 1988, abandoned.

FIELD OF THE INVENTION

The invention relates to a method of producing foreign gene products which comprises (1) transforming animal cells either (a) by using two plasmids, namely a plasmid containing the MMTV LTR and a foreign gene encoding a physiologically active substance inserted therein downstream from the LTR and a plasmid containing the LTR and a glucocorticoid receptor protein gene inserted therein downstream from the LTR, or (b) by using one plasmid comprising the LTR, a glucocorticoid receptor protein gene located downstream from the LTR, another LTR and a foreign gene encoding a physiologically active substance located downstream from the latter LTR, and (2) cultivating the transformed animal cells in a medium containing glucocorticoid in an amount effective for inducing mRNA transcription.

BACKGROUND OF THE INVENTION

In attempting to cause a cloned gene to be expressed in animal cells for the investigation of its function, it is sometimes difficult to obtain transformant cells due to the expression of said gene interfering with cell proliferation. To avoid such a problem it is necessary to have an expression system wherein the level of expression is low in a non-induced condition and wherein the desired gene expression can be effectively induced.

MMTV is a type of retrovirus or RNA virus. In MMTV-infected cells, the virus occurs as a provirus, namely in the form of a DNA integrated into the chromosomal DNA of the host cells. At each end of the thus-integrated DNA, there is an LTR which is about 1.3 kbp in length and composed of three regions, U3-R-U5. The two LTRs are in the same direction.

The LTR has both a promoter function and a transcription terminator function. In the U3 region of the LTR, there is a region capable of binding glucocorticoid receptor proteins (GRs) and this regulates the RNA synthesis. Thus, when a GR is bound to said region, the LTR promoter functions to initiate RNA synthesis, by which a protein is produced. However, the receptor (GR), when used alone, is incapable of binding; i.e., only the glucocorticoid-bound active form of GR can be bound to the receptor binding site of U3 to activate the LTR.

A system is already known which uses the mouse mammary tumor virus (MMTV) long terminal repeat (LTR) for glucocorticoid-induced expression of foreign genes [F. Lee et al., Nature, 294, 228–232 (1981)].

Since the maximum level of expression is restricted by the number of GR molecules naturally present in the cells, high level induction of the desired gene expressions which leads to large quantity production of the desired products has not been achieved.

SUMMARY OF THE INVENTION

It is an object of the invention to provide a method of producing infected cells suited for the production of a foreign gene, which comprises (1) transforming animal cells either (a) by using two plasmids, namely a plasmid containing the MMTV LTR (hereinafter "LTR") and a foreign gene (gene coding for a physiologically active substance) inserted therein downstream from said LTR and a plasmid containing the LTR and a GR gene inserted therein downstream from said LTR, or (b) by using a plasmid comprising the LTR, a glucocorticoid receptor protein gene located downstream from said LTR, another LTR and a foreign gene for the production of a physiologically active substance located downstream from the latter LTR.

Another object of the invention is to provide a superinduction method for producing physiologically active substances with good efficiency which comprises (1) culturing animal cells having a chromosome which contains the LTR, a foreign gene located downstream therefrom, another LTR and a GR gene located downstream from the latter LTR, and (2) adding a glucocorticoid to the resulting cultured cells so as to induce gene expression.

A further object of the invention is to provide plasmids and animal cells which are suited for use in carrying out the above methods.

DETAILED DESCRIPTION OF THE INVENTION

Figure 1:
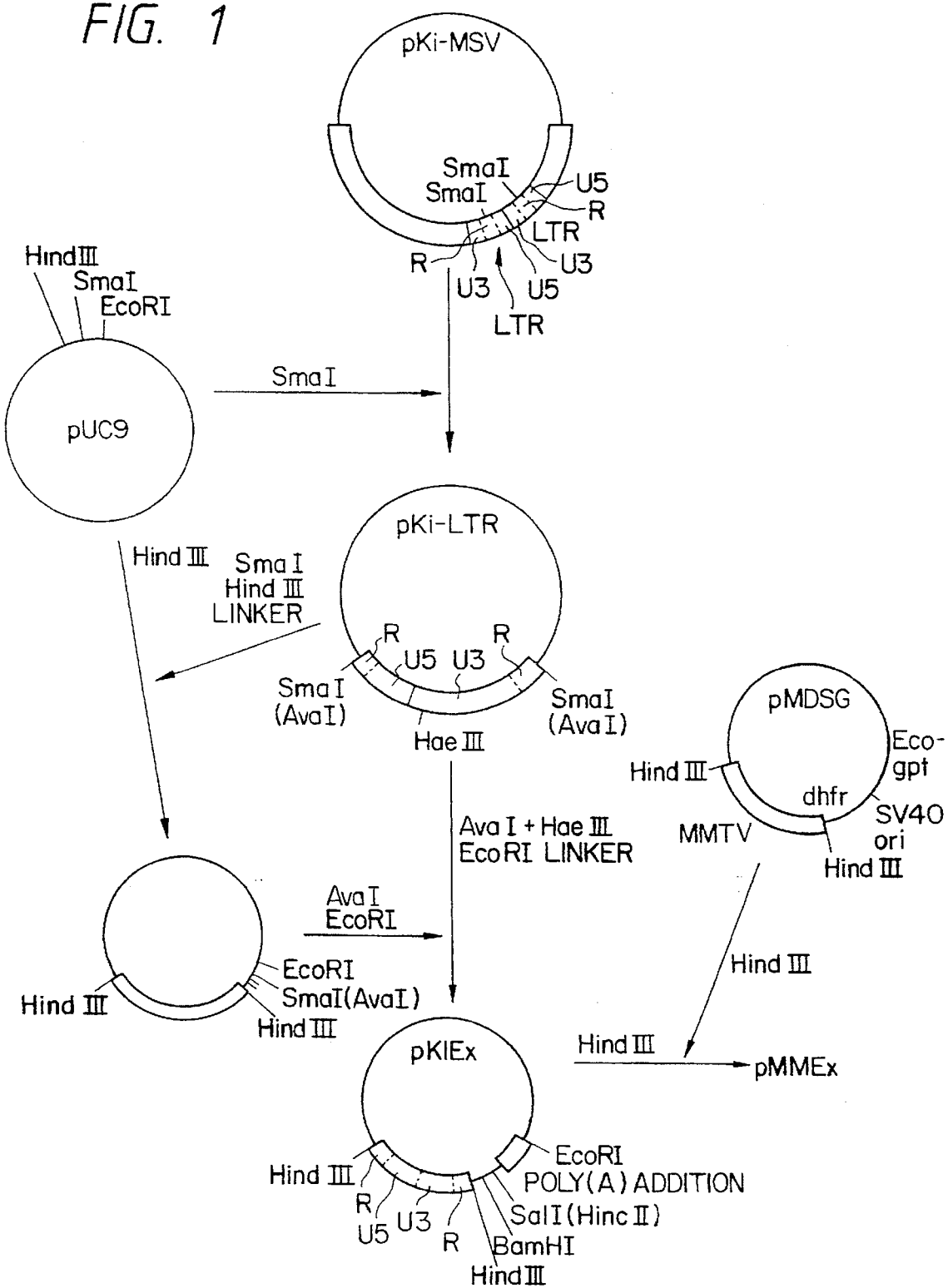
FIG. 1 shows a plasmid construction scheme for the plasmid pMDSG.

Two exemplary plasmids which have constructed in the present invention include a plasmid (pMMGR) containing the MMTV LTR, which is inducible by dexamethasone, a type of glucocorticoid, and a glucocorticoid receptor gene [rat glucocorticoid receptor gene; gift from Dr. K. R. Yamamoto; cf. Cell, 46, 389–399 (1986)] inserted therein downstream from said LTR and a plasmid (pMMgal) containing the MMTR LTR and the *Escherichia coli* β-gal gene inserted therein downstream from said LTR. When these plasmids were both transfected into mouse Ltk⁻ cells, a type of mammalian culture cell line, it was found that as compared with the case of carrying out transfection with pMMgal alone, the level of expression was equally low in the absence of dexamethasone but at least 100 times higher in the presence of dexamethasone.

Further, gene expression in a system containing a gene stably incorporated therein was confirmed by using a plasmid (pMMifα) containing the interferon α gene in lieu of the β-gal gene.

According to the present invention, since the cells capable of producing a desired substance contain the MMTV LTR, a GR gene located downstream from the LTR, another MMTV LTR, and a foreign gene coding for a desired substance located downstream from the latter LTR, the expression of a GR gene located downstream from the LTR is induced by glucocorticoid added so that the GR molecules present in the cells increase in number. Thus, the expression of a foreign gene coding for a desired substance can be induced at high level and the desired substance can be produced in large quantity.

Thus the invention provides:

(1) A plasmid which comprises the long terminal repeat (LTR) of mouse mammary tumor virus (MMTV) and a glucocorticoid receptor protein gene located downstream from said LTR;

(2) A plasmid which comprises the LTR of MMTV, a glucocorticoid receptor protein gene located downstream from said LTR, another LTR of MMTV and a foreign gene coding for a physiologically active substance located downstream from the latter LTR;

(3) A method of producing cells capable of producing a physiologically active substance which comprises cotransfecting an animal cell with (a) a plasmid comprising the LTR of MMTV and a glucocorticoid receptor protein gene located downstream of said LTR, and (b) a plasmid comprising the LTR of MMTV and a foreign gene coding for a physiologically active substance located downstream from the latter LTR;

(4) A method of producing cells capable of producing a physiologically active substance which comprises transfecting an animal cell with a plasmid comprising the LTR of MMTV, a glucocorticoid receptor gene located downstream from said LTR, another LTR and a foreign gene coding for a physiologically substance located downstream from the latter LTR;

(5) An animal cell cotransfected with (a) a plasmid comprising the LTR of MMTV and a glucocorticoid receptor protein gene located downstream from said LTR, and (b) a plasmid comprising the LTR of MMTV and a foreign gene coding for a physiologically active substance located downstream from said LTR;

(6) An animal cell bearing, on a chromosome thereof, the LTR of MMTV, a glucocorticoid receptor protein gene located downstream from said LTR, another LTR of MMTV and a foreign gene coding for a physiologically active substance located downstream from the latter LTR;

(7) An animal cell transfected with a plasmid comprising the LTR of MMTV, a glucocorticoid receptor protein gene located downstream from said LTR, another LTR of MMTV and a foreign gene coding for a physiologically active substance located downstream from the latter LTR;

(8) A method of producing foreign gene products which comprises (1) cotransfecting an animal cell with (a) a plasmid comprising the LTR of MMTV and a glucocorticoid receptor protein gene located downstream from said LTR, and (b) a plasmid comprising the LTR of MMTV and a foreign gene coding for a physiologically active substance located downstream from the latter LTR, and (2) propagating the thus-obtained transfected cell in the presence of a glucocorticoid so as to induce expression of said physiologically active substance; and (9) A method of producing foreign gene products which comprises propagating an animal cell bearing, on a chromosome thereof, the LTR of MMTV, a glucocorticoid receptor protein gene located downstream from said LTR, another LTR of MMTV and a foreign gene coding for a physiologically active substance in the presence of a glucocorticoid so as to induce expression of said physiologically active substance.

The foreign gene products to be produced in accordance with the present invention includes various physiologically active substances, such as lymphokines, hormones, antigenic proteins, peptides (e.g., tPAs) and glycopeptides. The foreign genes coding for such substances can be obtained and used by methods well known in the art.

The LTR of MMTV is already known [cf. J. Virol., 37, 226–238 (1981) and Nature, 294, 228–232 (1981)].

The glucocorticoid receptor protein and the gene coding therefor are also well known [cf. Cell, 46, 389–399 (1986)].

The plasmids to be used practicing the invention can be constructed in a conventional manner. An example will be given later herein for the case where two plasmids are employed.

Transfection of a cell with an induction plasmid (containing the LTR and a GR gene) and a production plasmid (containing the LTR and the foreign gene coding for a desired product) results in incorporation of the LTR-GR gene and the LTR-desired product gene into a chromosome of said cell. For transfection, the two plasmids may be used either simultaneously or separately. It is of course possible to perform transfection using a single plasmid with both the two genes inserted therein.

The plasmid containing an induction gene and a production gene can be constructed by ligating an induction plasmid and a production plasmid each of which is previously cleaved with appropriate restriction enzymes.

The induction plasmid and the production plasmid introduced into a chromosome of an animal cell may be located adjacent to, or at a distance from, each other. The plasmids may also be located on different chromosomes.

When the transformant cells are cultured in a glucocorticoid-containing medium, (1) The glucocorticoid binds the receptor protein (GR) occurring in a slight amount in the cytoplasm to give rise to an activated form of the receptor.

(2) The active-form receptor arrives at the nucleus and is bound to the receptor binding site in U3 of the MMTV LTR on the chromosome.

(3) Then, the LTR promoter comes into function, whereby the gene downstream therefrom is expressed and the GR protein is produced. (The desired protein is also produced in a slight amount.)

(4) The GR protein produced binds the glucocorticoid to give an additional amount of active-form receptor. Repetition of steps (2)-(4) results in production of the GR protein in an increased amount in the system and thus leads to production of the desired protein in a large amount.

Tranfection of cells with the plasmid or plasmids can be performed by any conventional method, for example the calcium phosphate method. When two plasmids are used, the plasmid for desired substance production is used in an amount of from about 0.1 to 10 mol, preferably about from 1 to 10 mol, per mol of the GR gene-containing plasmid.

As the cells, various culture cell lines established for various purposes and currently available may be used. For example, there may be mentioned BHK 21 (baby hamster kidney-derived fibroblast-like culture cell line), CV-1 (monkey kidney-derived fibroblast-like culture cell line) and HeLa tk⁻ (human cervical cancer-derived culture cell line), among others. Cell culturing can be conducted using media and procedures known for the respective cell lines.

Cells with the gene in question and others incorporated therein can be selected by any method generally employed in the field of art. Thus, for example, when a plasmid containing an antibiotic inactivation enzyme gene inserted downstream from the SV40 promoter is used as a selection marker in admixture with the plasmid or plasmids according to the invention and resistant strains are selected in a medium containing the relevant antibiotic, strains with the plasmid(s) incorporated in a chromosome can be obtained. It is of course possible to carry out selection by inserting a gene for selection into one of the plasmids according to the invention.

The glucocorticoid to be used for the purpose of induction can be selected from among, for example, those known in the art or described in the literature, such as dexamethasone, cortisones, hydrocortisones and dehydrocortisones.

The glucocorticoid is added to the culture medium to give a final concentration of $10^{-6}$ to $10^{-7}$M.

The following examples are for illustration purpose only and are in no way intended to limit the scope of the present invention.

EXAMPLE 1

Construction of Expression Vector pMMEx

The Ki-MSV plasmid clone 4 [N. Tsuchida et al., J. Virol., 38, 720 (1981)] was cleaved with SmaI and a promoter-containing fragment (about 0.6 kbp) was isolated by agarose gel electrophoresis. The fragment was ligated, in the presence of T4 ligase, into pUC9 (Pharmacia) previously cleaved with SmaI. The resultant recombinant plasmid was used to transform *Escherichia coli* (hereinafter *E. coli*) HB101. The plasmid thus obtained was named pKi-LTR (see FIG. 1).

The plasmid pKi-LTR was cleaved with SmaI and ligated to a 5'-phosphorylated HindIII linker in the presence of a ligase, followed by cleavage with HindIII. A U3 (promoter) -containing fragment was isolated by agarose gel electrophoresis and ligated, in the presence of T4 ligase, into pUC9 previously cleaved with HindIII. The ligation mixture was used to transform *E. coli* HB101, and a plasmid with said fragment inserted therein was obtained (see FIG. 1) The plasmid was cleaved with AvaI and EcoRI. Separately, pKi-LTR was cleaved with AvaI and HaeIII, the EcoRI linker was added and cleavage with EcoRI was carried out for conversion of the HaeIII end (blunt end) to an EcoRI end to obtain a poly(A) addition region (U5)-containing fragment (about 0.25 kbp). The thus-obtained fragment was ligated to the above-mentioned pUC9-derived fragment in the presence of T4 ligase. The ligation mixture was used to transform *E. coli* HB101, and a plasmid with the fragment inserted was obtained and named pKIEx (see FIG. 1).

The plasmid pMDSG [F. Lee et al., Nature, 294, 228 (1981)] was cleaved with HindIII, and an MMTV promoter-containing fragment (about 1.4 kbp) was isolated by agarose gel electrophoresis. Separately, pKIEx was cleaved with HindIII, a larger fragment no longer having the pKi-LTR-derived promoter was isolated and ligated to the above-mentioned 1.4 kbp fragment in the presence of T4 ligase. The resultant recombinant plasmid was used to transform *E. coli* HB101, and an plasmid, pMMEx, with the MMTV promoter fragment inserted therein was obtained (see FIG. 1).

EXAMPLE 2

Construction of Expression Vectors pMMGR and pMMifα

Figure 2:
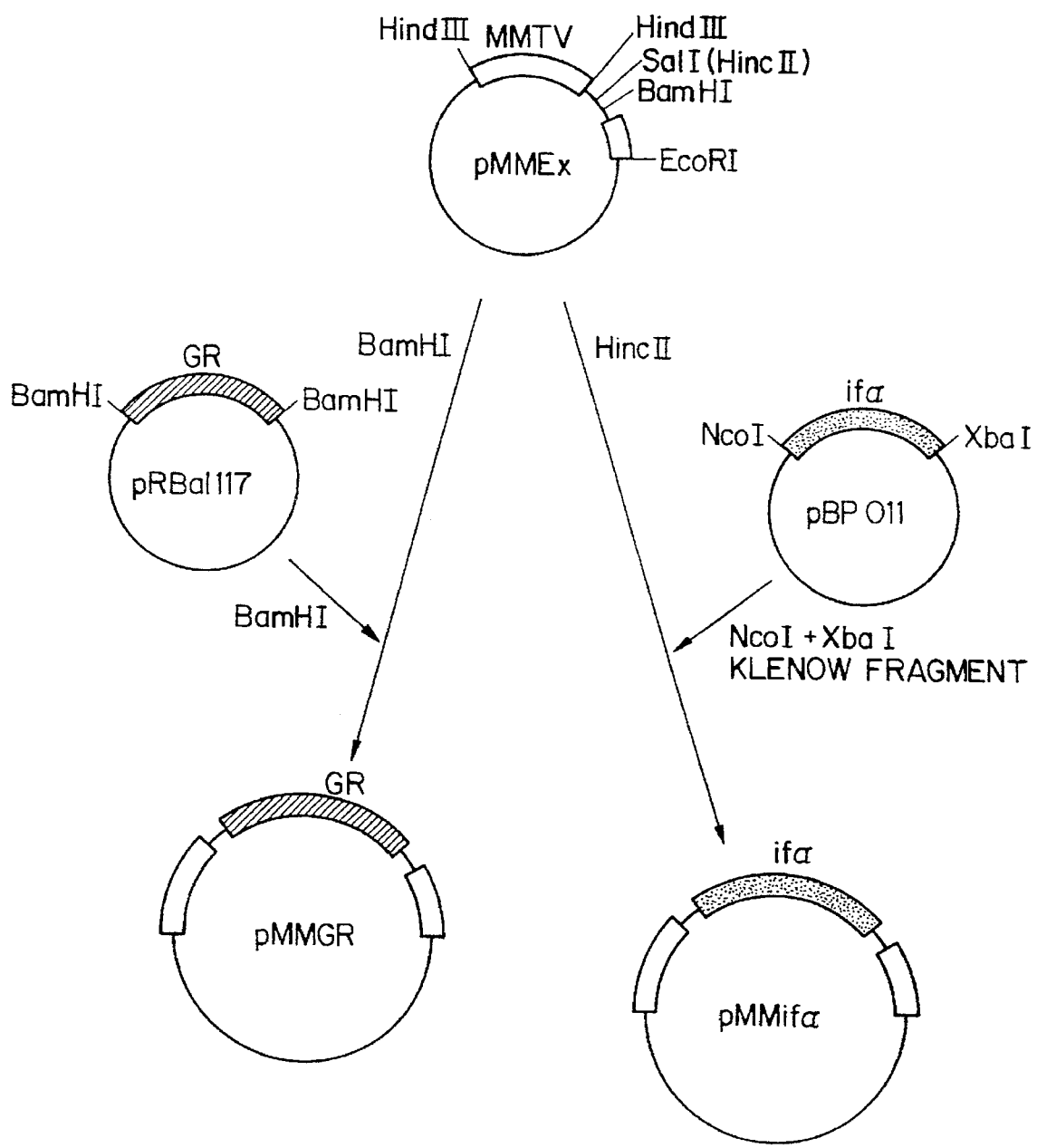
FIG. 2 shows a plasmid construction scheme for the plasmids pMMGR and pMMifα.

The plasmid pRBal 117 [R. Miesfeld et al., *Cell*, 46, 389 (1986)] was cleaved with BamHI, and a rat corticoid receptor gene-containing fragment (about 2.8 kbp) was isolated by agarose gel electrophoresis. The fragment was ligated, in the presence of T4 ligase, into pMMEx previously cleaved with BamHI, the ligation mixture was used to transform *E. coli* HB101, and a plasmid with the receptor gene inserted therein, pMMGR, was obtained (see FIG. 2). A strain harboring said plasmid, namely *E. coli* pMMGR, has been deposited at the Fermentation Research Institute, Agency of Industrial Science and Technology, Japan, under the deposit number FERM BP-2052 in accordance with Budapest treaty.

The interferon α gene (ifα)-containing plasmid pBP011 (cf. Reference Example) was cleaved with NcoI and XbaI, and an ifα-containing fragment (0.5 kbp) was isolated by agarose gel electrophoresis. This fragment was rendered blunt-ended by treatment with DNA polymerase I Klenow fragment in the presence of dNTP's and then ligated to pMMEx previously cleaved with HincII, whereby a plasmid, pMMifα, with the gene inserted therein was obtained (see FIG. 2). A strain harboring said plasmid, namely *E. coli* MMifα, has been deposited at the Fermentation Research Institute under the deposit number FERM BP-2053 in accordance with Budapest treaty.

EXAMPLE 3

Expression of Interferon α in L Cells

Ltk⁻ cells of a mouse fibroblast-like cell line were grown on MEM (Eagle's minimum essential medium) supplemented with 10% (v/v) FCS (fetal calf serum) to $1 \times 10^6$ cells per dish. Medium exchange with fresh medium was carried out 4 hours before transnfection. A mixed solution of the following three plasmids was prepared:

|  |  | (Mole ratio) |
|---|---|---|
| pSV2neo (ATCC 37140) | 0.5 µg | (1) |
| pMMGR | 33 µg | (50) |
| PMMifα | 5 µg | (1) | pSV2neo, a plasmid containing a gene coding for neomycin inactivating enzyme, which can serve as a selection marker, was obtained from the ATCC. To the mixture was added 11.5 µg of a carrier DNA (bovine thymus DNA). Water was added to make the total volume 2.2 ml and, then, 300 µl of 2M calcium chloride was added to give solution I. Solution II was prepared which had the following composition:

| 2 × HBS (HEPES 10 g/l-sodium chloride 16 g/l) | 2.5 ml |
|---|---|
| 100 × phosphate buffer (70 mM Na₂HPO₄-70 mM NaH₂PO₄) | 50 µl |

Solution I and solution II were mixed together slowly to give a suspension. After 30 minutes of standing, 1 ml of the suspension was transferred to a dish containing the above-mentioned Ltk⁻ cells growing therein.

After 12 hours, the medium was replaced with fresh medium. After 2 further days, cultivation was started in a medium containing 0.4 g (potency: calculated based on the antimicrobial activity) per liter of G418 (Gibco), a neomycin-like antibiotic, and continued with medium exchange at 3- to 4-day intervals. Colonies found 2 weeks after DNA introduction were transferred to a 96-well microwell plate. When the wells were each full of cells (confluent), the medium was replaced with a medium containing $1 \times 10^{-6}$M dexamethasone. Two days thereafter, an interferon activity assay was done according to the method as described in P. C. Familletti et al., Meth. Enzym., 78, 387 (1981).

Among the clones thus obtained, the six colonies having the highest level of activity were selected and transferred to dishes (35 mm in diameter). After growing in the dishes almost to confluence, growing was repeated almost to confluence in two 35-mm dishes for each clone. Then, dexamethasone was added to one of the two dishes to a concentration of $1\times10^{-6}$M. The dexamethasone-supplemented medium and the dexamethasone-free medium were assayed for interferon activity 48 hours after addition of dexamethasone.

Five out of 51 clones showed an interferon activity of not less than $10^4$ U/ml, with a frequency of about ⅒. The activity range $10^3$ to $5\times10^3$ U/ml had the highest frequency (25 clones). For those clones which showed an activity exceeding $10^4$ U/ml, the activity data obtained in the presence of dexamethasone (+dex) and in the absence thereof (dex−) are shown in the Table below.

The number of copies inserted into chromosomes was examined by isolating the chromosomal DNA of the clone Lif10 and of the clone Lif41 and by performing cleavage with BamHI, BamHI+PstI, and EcoRI, agarose gel electrophoresis, blotting on nitrocellulose and hybridization with pMMGR and pMMifα. For both clones, the copy number was found to be about 100 for each of the GR gene and the interferon α gene.

TABLE

| Clone No. | +dex ($10^{-6}$ U/ml) | −dex (U/ml) | Relative induction (times) |
|---|---|---|---|
| Lif10 | $2.17 \times 10^4$ | $1.32 \times 10$ | 1640 |
| Lif15 | $1.06 \times 10^4$ | <2 | >5300 |
| Lif41 | $2.27 \times 10^4$ | <2 | >11350 |
| Lif46 | $1.71 \times 10^4$ | <2 | >8550 |
| Lif49 | $2.31 \times 10^4$ | <2 | >11550 |
| Lif50 | $9.77 \times 10^3$ | <2 | >4890 |

Note: "<2" means "below the detection limit".

EXAMPLE 4

Figure 3:
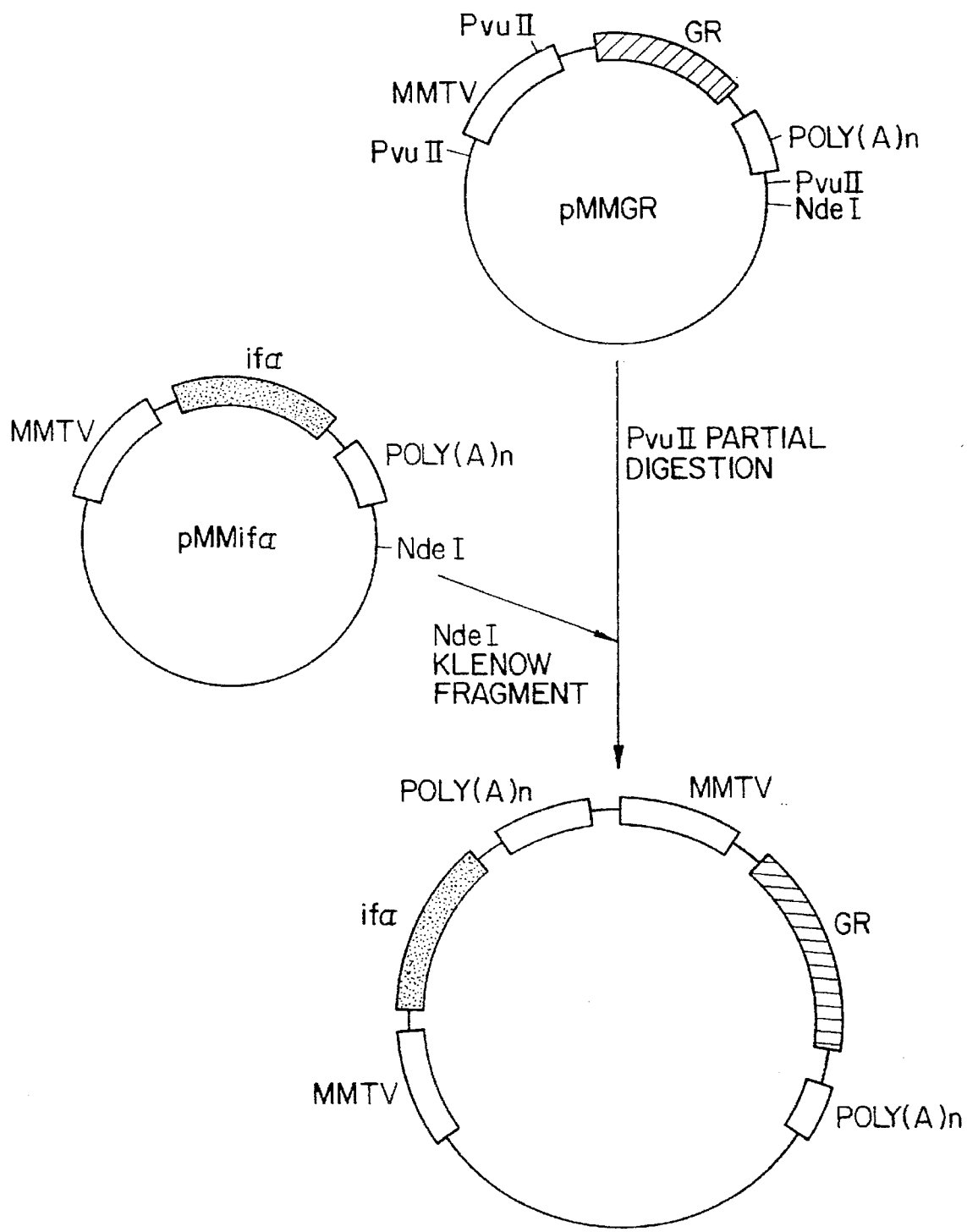
FIG. 3 shows a plasmid construction scheme for the plasmid with an induction gene and a production gene.

Construction of Expression Vector Containing an Induction Gene and a Production Gene The plasmid pMMGR obtained in Example 2 was partially digested with PvuII and a plasmid containing an MMTV-LTR, a GR gene and a poly(A) addition region (about 4.8 kbp) was isolated by agarose gel electrophoresis. Separately, the plasmid pMMifα obtained in Example 2 was cleaved with NdeI, followed by treating with DNA polymerase I Klenow fragment in the presence of dNTP's to render the cleaved end blunt. The DNA fragment was ligated to the above-mentioned 4.8 kbp fragment in the presence of T4 ligase. The resultant recombinant plasmid was used to transform *E. coli* HB101 and a plasmid with an induction gene and a production gene was obtained (FIG. 3).

REFERENCE EXAMPLE

Construction of the Plasmid pBP011

The plasmid pBM034 [Agric. Biol. Chem. 51(6), 1573–1580 (1987)] was cleaved with XbaII and HpaII, and an interferon α gene (ifα)-containing fragment lacking the initiation codon ATG (about 570 bp) was isolated by agarose gel electrophresis. Separately, the following DNA fragments, Pr-B-11 and Pr-B-12, were chemically synthesized.

```
Pr-B-11:  5'-ATGCCGAATTATTCATACACCCCA CCATGGCC-3'
Pr-B-12:  3'-TACGGCTTAATAAGTATGTGGGGTGGTA CCGGGC-5'
                                           NcoI  (HpaII)
```

The fragments were complementary to each other so that they could form double-stranded DNA. Further, the fragments possessed an NcoI-cleavage site and were capable of binding to a HpaII-cleavage site of another DNA fragment at one end. Pr-B-12 was phosphorylated at the 5'-end thereof in the presence of T4 kinase and annealed with Pr-B-11 to form a double-stranded DNA.

Figure 4:
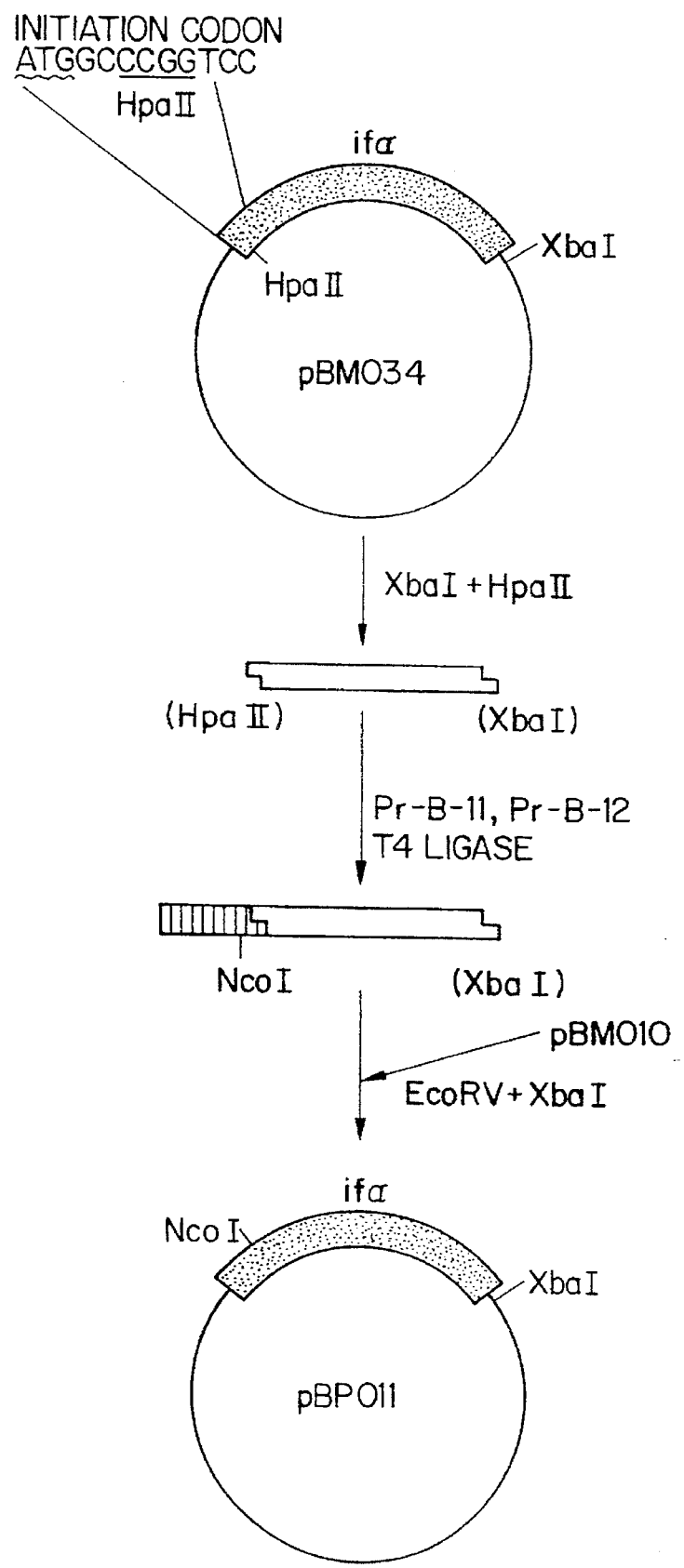
FIG. 4 shows a plasmid construction scheme for the plasmid pBM011.

The thus-obtained annealed fragment was ligated with the above-described ifα-gene-containing fragment in the presence of T4 ligase an about 600 bp DNA fragment was obtained by agarose gel electrophoresis. Then, the resultant DNA fragment was phosphorylated in the presence of T4 kinase, followed by ligating with the plasmid pBM010 (vide supra) previously cleaved with EcoRV and XbaI in the presence of T4 ligase. The recombinant plasmid thus obtained was used to transform *E. coli* HB101, and the plasmid obtained from transformants was named pBP011 (FIG. 4).

The superinduction method according to the invention has the following advantageous features:

(i) In an uninduced state, the expression level is very low. The property is advantageous in cases where the expression product is toxic to the cells. That is, in systems in which gene products are formed continuously, such as conventional high expression systems, gene incorporation into cells will result in expression of cytotoxic substances and the cells will not be capable of further growth or will die, leading to failure in cell cloning. On the contrary, in the superinduction system of the present invention where the expression level is very low in an uninduced state, cells can be cloned without causing any damage to them and induction can be effected after mass culturing of the cells. Therefore, the method is suited for large quantity production of the desired substance.

(ii) Clones showing relative induction of ten thousand times or more can be obtained in the present invention. Among the thus-far known systems for inducible gene expression, the one highest in relative induction is perhaps a system involving MMTV and, in some cell clones, gene expression can be induced at a level of almost 1,000 times on the mRNA level. However, this applies only to those cases where the virus itself is incorporated into cells. When cells are transfected with a recombinant derived from MMTV by insertion of a marker gene downstream therefrom, the relative induction is at most several tens of times, although it may vary depending on the cells. Although the superinduction system according to the invention is similar with the latter case in that the gene coding for the desired product is inserted downstream from MMTV for transfection, a very high level of induction can be achieved in a superinduction system of the present invention. The higher the relative induction is, the higher the maximum production level is. Hence, the superinduction method is advantageous for large quantity production.

While the invention has been described in detail and with reference to specific embodiments thereof, it will be apparent to one skilled in the art that various changes and modifications can be made therein without departing from the spirit and scope thereof.

What is claimed is:

1. A method of producing gene products in mammalian cells comprising:
   (1) transfecting mammalian cells with both:
      (a) a first expression plasmid, comprising a mouse mammary tumor virus (MMTV) long terminal repeat (LTR) operably linked to a glucocorticoid receptor protein gene (GRP), wherein on transfection said cells produce glucocorticoid receptor protein as a result of expression of said first expression plasmid; and (b) a second expression plasmid, comprising an MMTV LTR operably linked to a gene encoding a physiologically active substance, wherein on transfection said cell produces said physiologically active substance as a result of expression of said second expression plasmid;

wherein on exposing the resulting transfected cells to a glucocorticoid, transfected mammalian cells that exhibit greater expression of said physiologically active substance in the presence of said glucocorticoid than in the absence thereof are selected;

(2) propagating the thus-obtained transfected cells in the presence of said glucocorticoid to induce expression of said physiologically active substance; and (3) obtaining said physiologically active substance.

2. A method of producing foreign gene products in mammalian cells bearing, on a chromosome thereof:

(a) a first mouse mammary tumor virus (MMTV) long terminal repeat (LTR) operably linked to a glucocorticoid receptor protein gene (GRP), wherein on transfection said cells produce glucocorticoid receptor protein as a result of expression of said first MMTV LTR operably linked to said GRP gene; and (b) a second MMTV LTR operably linked to a gene encoding a physiologically active substance, wherein on transfection said cells produce said physiologically active substance as a result of expression of said second MMTV LTR operably linked to said gene encoding said physiologically active substance;

wherein on exposing the resulting transfected cells to a glucocorticoid, transfected mammalian cells that exhibit greater expression of said physiologically active substance in the presence of said glucocorticoid than in the absence thereof are selected, comprising:

(1) propagating said cells in the presence of said glucocorticoid to induce expression of said physiologically active substance; and (2) obtaining said physiologically active substance.

3. The method of claim 2, wherein said first plasmid is in a chromosome of said cells and said second plasmid is in a chromosome of said cells.

4. The method for producing foreign gene products as claimed in claim 1, wherein said glucocorticoid is selected from the group consisting of dexamethasone, a cortisone, a hydrocortisone and a dehydrocortisone.

5. The method for producing foreign gene products as claimed in claim 2 wherein said glucocorticoid is selected from the group consisting of dexamethasone, a cortisone, a hydrocortisone and a dehydrocortisone.

\* \* \* \* \*